(12) United States Patent
Tapsak

(10) Patent No.: US 8,691,975 B2
(45) Date of Patent: Apr. 8, 2014

(54) SOLVENT-FREE MECHANOCHEMICAL PURIFICATION OF COMPOUNDS

(75) Inventor: Mark Allan Tapsak, Orangeville, PA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/637,249

(22) PCT Filed: Jun. 4, 2012

(86) PCT No.: PCT/US2012/040727
§ 371 (c)(1),
(2), (4) Date: Sep. 25, 2012

(87) PCT Pub. No.: WO2013/184091
PCT Pub. Date: Dec. 12, 2013

(65) Prior Publication Data
US 2013/0324712 A1    Dec. 5, 2013

(51) Int. Cl.
*C07H 1/06*    (2006.01)
(52) U.S. Cl.
CPC .................................. *C07H 1/06* (2013.01)
USPC ...................................................... 536/119
(58) Field of Classification Search
CPC ........................................................ C07H 1/06
USPC ...................................................... 536/119
See application file for complete search history.

(56) References Cited

U.S. PATENT DOCUMENTS

| | | | |
|---|---|---|---|
| 4,316,852 | A | 2/1982 | Blachford |
| 5,318,794 | A | 6/1994 | Richards |
| 6,730,812 | B2 | 5/2004 | Pecharsky et al. |
| 7,105,714 | B2 | 9/2006 | Pecharsky et al. |
| 2007/0155677 | A1 | 7/2007 | Heikkila et al. |
| 2010/0015028 | A1 | 1/2010 | Johnson et al. |

OTHER PUBLICATIONS

Whistler et al. aldchydo-D-Galactose Heptaacetate and aldehydo-D-Xylose Hexaacetate from Acetolysis of Guaran and Xylan.*
Wu et al. Solid silica sulfuric acid (SSA) as a novel and efficient catalyst for acetylation of aldehydes and sugars. Tetrahedron 62:7995-7998, 2006.*
Pirie NW. The Hyperacetylation of Aldoses. Biochem J 30(3): 374-376, 1936.*
Whistler et al. aldchydo-D-Galactose Heptaacetate and aldehydo-D-Xylose Hexaacetate from Acetolysis of Guaran and Xylan. J Am Chem Soc 71:1476-1477, 1949.*
International Search Report and Written Opinion for PCT/US2012/040727 dated Aug. 21, 2012.
Korolev et al., Mechanochemical Transformations of the Crystalline Anomers of D-Glucose, *Chemistry for Sustainable Development* (2004), 3:339-346 (Abstract).
Lyakhov et al., Mechanochemical Synthesis of Organic Compounds and Composites with Their Participation, *Russian Chemical Reviews* (2010), 79(3):189-203 (Abstract).
Medvedeva et al., Structural Transformations of Siberian Larch Arabinogalactan at Mechanochemical Treatment and Biological Properties of Products, *Chemistry of Plant Raw Material* (2009), 3:49-56 (Abstract).
Mugunthan et al., Application of Ball Milling Technology to Carbohydrate Reactions-II. Solvent-free Mechanochemical Synthesis of Glycosyl Azides, *Journal of Carbohydrate Chemistry* (2008), 27(5):294-299 (Abstract).
Patil et al., Application of Ball Milling Technology to Carbohydrate Reactions, Part 1. Regioselective Primary Hydroxyl Protection of Hexosides and Nucleoside by Planetary Ball Milling, *ChemInform* (Dec. 18, 2008), 40(3) (Abstract).
Patil et al., Solvent-free synthesis of thioglycosides by ball milling, *Green Chem.* (Apr. 24, 2009), 11:953-956 (Abstract).
Rothenberg et al., Understanding Solid Solid Organic Reactions, *J. Am. Chem. Soc.* (Aug. 16, 2001), 123(36):8701-8708 (Abstract).
Wang et al., Facile Preparation of Peracetates and Per-3-bromobenzoates of α-Mono- and Disaccharides, *Molecules* (Oct. 31, 2005), 10:1325-1334.

* cited by examiner

*Primary Examiner* — Brandon Fetterolf
*Assistant Examiner* — Yih-Horng Shiao
(74) *Attorney, Agent, or Firm* — Pepper Hamilton LLP

(57) ABSTRACT

Methods for purifying and extracting compounds from a mixture are provided using a solvent-free mechanochemical method. Methods for purifying and/or extracting sugars, amino acids, and, the like, from a mixture are also provided, using a solvent-free mechanochemical method.

23 Claims, 2 Drawing Sheets

SOLVENT-FREE MECHANOCHEMICAL PURIFICATION OF COMPOUNDS

This application is a U.S. national stage filing under 35 U.S.C. §371 of International Application No. PCT/US2012/040727 filed Jun. 4, 2012, entitled "Solvent-Free Mechanochemical Purification Of Compounds," which is incorporated by reference in its entirety.

FIELD

Solvent-free mechanochemical compound purification methods are provided.

BACKGROUND

Mixtures of compounds can be difficult to separate because of similarities in physical properties. These similarities can require the use of inefficient methods to separate the compounds, which can result in higher costs for the final products. For example, mixtures of sugars need to be separated to produce chemical feedstocks, however, current methodology is inefficient and requires the use of solvents that can be harmful to the environment. Thus, there is a need for more efficient methods of separating and/or purifying compounds from a mixture. The methods of the present disclosure fulfill these needs as well as others.

SUMMARY OF THE INVENTION

In some embodiments, methods of purifying compounds are provided. In some embodiments, the method comprises providing a mixture comprising a first compound and a second compound, wherein the first compound has a first melting point, the second compound has a second melting point, and the first melting point is lower than the second melting point; derivatizing the first compound in a solvent-free mechanochemical process to produce a first derivatized compound, wherein the derivatizing step is performed at a temperature less than the second melting point; and purifying the first derivatized compound from the mixture. In some embodiments, the first compound and the second compound is independently a carbohydrate, amino acid, lipid, hydrocarbon, nucleic acid, or peptide.

In some embodiments, the derivatizing step comprises contacting the first compound with an acid or alcohol to produce the first derivatized compound. In some embodiments, the purifying step comprises purifying the first derivatized compound by extraction, liquid chromatography, recrystallization, or any combination thereof.

In some embodiments, the purifying step comprises hydrolyzing the first derivatized compound to yield a first purified compound.

In some embodiments, the mixture comprises a third compound having a third melting point, wherein the second melting point is lower than the third melting point, the method further comprising: derivatizing the second compound in a solvent-free mechanochemical process to produce a second derivatized compound, wherein the derivatizing step is performed at a temperature less than the third melting point; and purifying the second derivatized compound from the mixture.

In some embodiments, the method further comprises derivatizing another compound with the lowest melting point after purifying the derivatized first compound to yield a derivatized another compound, wherein the another compound has a higher melting point than the first compound; and purifying the derivatized another compound.

In some embodiments, a method of purifying a compound from a mixture of a plurality of compounds, is provided the method comprising providing a mixture of a plurality of compounds, each of the plurality of compounds having a different melting point, wherein the mixture comprises a first compound having a first melting point, wherein the first melting point has the lowest melting point of the different melting points of the compounds; isolating the first compound having the lowest melting point by derivatizing the first compound having the lowest melting point of the plurality of compounds in a solvent-free mechanochemical process to produce a first derivatized compound, wherein the derivatizing step is performed at a temperature less than a melting point of another compound present in the mixture, wherein the melting point of the another compound is higher than the first melting point; and purifying the first derivatized compound from the mixture; optionally repeating the steps to purify each compound present in the mixture of the plurality of compounds, wherein the compounds are purified in ascending order of melting point.

DETAILED DESCRIPTION

Figure 1:
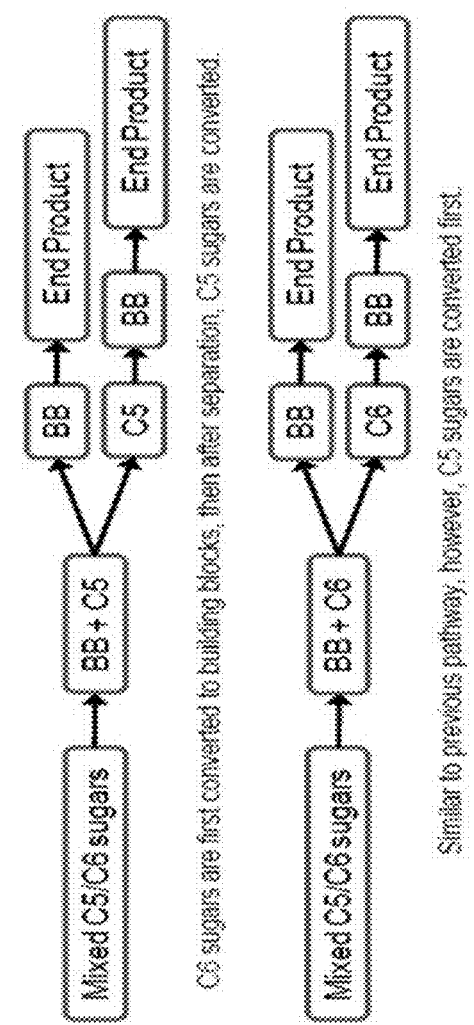
FIG. 1 illustrates a non-limiting example of a solvent free mechanism for separating compounds.
Figure 2:
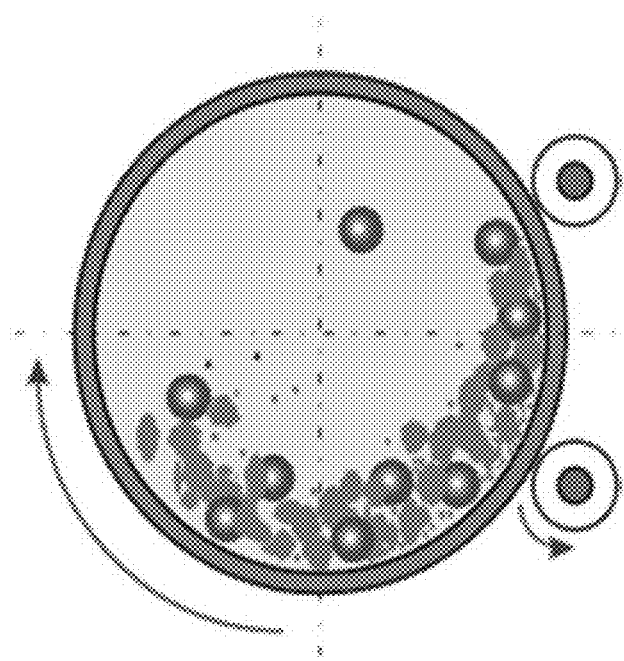
FIG. 2 illustrates a non-limiting example of a ball mill that can be used to provide mechanochemical energy.

This description is not limited to the particular processes, compositions, or methodologies described, as these may vary. The terminology used in the description is for the purpose of describing the particular versions or embodiments only, and it is not intended to limit the scope of the embodiments described herein. Unless defined otherwise, all technical and scientific terms used herein have the same meanings as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

It must also be noted that as used herein and in the appended claims, the singular forms "a", "an", and "the" include plural reference unless the context clearly dictates otherwise.

As used in this document, terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Embodiments described herein provide methods of purifying or isolating compounds from a mixture based upon differences in their melting points. The compounds can, for example, be separated by derivatizing the different compounds in the mixture at different temperatures. The temperatures at which the compounds can be derivatized can be, for example, below the melting point of one compound, below the boiling point of the mixture, or below the eutectic point of the mixture. The melting point of a particular compound, however, can be affected by its surrounding, that is the presence of other compounds present in the composition. Therefore, the melting point temperature of a pure compound may not be the melting point temperature at which the methods are performed at or around. Instead the melting points may be the temperature that the compound melts in the presence of the other compounds or impurities in the mixture. Thus, in some embodiments, the temperature that is used as a reference is the eutectic point of the mixture.

In some embodiments, the method comprises derivatizing a first compound present in a mixture, wherein the mixture comprises at least the first compound and a second compound, wherein the first compound has a first melting point and the second compound has a second melting point, and the first melting point is lower than the second melting point. The derivatizing can be performed in a solvent-free mechanochemical process to produce the first derivatized compound. In some embodiments, the derivatizing step is performed at a temperature equal to or greater than the first melting point. In some embodiments, the derivatizing step is performed at a temperature that is less than the second melting point. In some embodiments, the derivatizing step is performed at a temperature less than the first melting point. In some embodiments, the derivatizing step is performed at a temperature that is less than the boiling point of the mixture. In some embodiments, the derivatizing step is performed a temperature that is less than the eutectic point of the mixture.

In some embodiments, the derivatizing step is performed at room temperature. In some embodiments, the derivatizing step is performed at a temperature of about 25 degrees Celsius. In some embodiments, the derivatizing step is performed at a temperature of about 20 to about 30 degrees Celsius, about 20 to about 25, about 25 to about 30 degrees Celsius. In some embodiments, the derivatizing step is performed at a temperature that is less than 30 degrees Celsius. In some embodiments, the derivatizing step is performed at a temperature of about 20 degrees Celsius, at about 25 degrees Celsius, about 30 degrees Celsius, or in a range between any two of these values.

In some embodiments, the derivatizing step is done under a vacuum. In some embodiments, the derivatizing step is done under decreased pressure. The decreased pressure can be, for example, less than atmospheric pressure, which is about 101 kPa.

The methods described herein can be used to purify many types of compounds from a mixture. Examples of compounds that can be purified or isolated from a mixture include, but not limited to, carbohydrates, amino acids, lipids, hydrocarbons, nucleic acid molecules, proteins, or peptides. Examples of carbohydrates include, but are not limited to, C5 sugars, C6 sugars, and the like. In some embodiments the carbohydrate is arabinose, galactose, glucose, or mannose.

The compounds present in the mixture can be present in various types of mixtures. In some embodiments, the mixture is a waste stream that includes organic compounds, such as but not limited, to sugars, amino acids, and the like. Examples of mixtures include, but are not limited to, black liquor. Black liquor is a waste product that is generated in the paper pulping industry, from bio-refineries and other waste streams. In some embodiments, the mixture is a "sugar rich biorefining waste" or "sugar rich biorefining waste product." That is the mixture can be a mixture of sugars. The methods described herein can be used to isolate and purify compounds present in the black liquor. Therefore, the methods described herein can be used to recycle portions of the waste products, thereby making the processes more efficient, and cost, effective. In some embodiments, the black liquor comprises arabinose, galactose, glucose, mannose, or any combination thereof. In some embodiments, the first compound to be derivatized is mannose. In some embodiments, the second compound is arabinose, galactose, or glucose. However, any compound present in a mixture can be the first compound.

The derivatizing step adds a "group" to the compound of interest being isolated or purified from the mixture. The group can be an alcohol or an acid. In some embodiments, the group is an alkyl alcohol, such as but not limited to, $C_1$-$C_8$ alkyl alcohol. In some embodiments, the alcohol is a $C_2$-$C_4$ alkyl alcohol or a $C_5$-$C_8$ alkyl alcohol. In some embodiments, the alcohol or acid is methanol, ethanol, butanol, isobutanol, isopropanol, stearic alcohol, stearic acid, acetic acid, acyl chloride, or any combination thereof. The length of the alkyl chain will alter the properties of the compound. The longer the chain the more non-polar the derivatized compound will become. These differences in the physical properties of the derivatized compound can then be used to isolate the derivatized compound from the mixture of compounds.

In some embodiments, the method further comprises purifying or isolating the first derivatized compound. The first derivatized compound can then be converted back to the first compound without the derivative group that was added in the reaction described above. The purifying step can be done by a variety of methods such as, hot not limited to, extraction, column chromatography, recrystallization, or any combination thereof. The column chromatography can be done, for example, in a HPLC system. For example, the differences in the polarity of the compounds can be used to separate the compounds in the HPLC system.

In some embodiments, the purifying step comprises hydrolyzing the derivatized compound to yield the purified compound. Other methods of removing the group that was added during the derivatizing step can also be used.

In some embodiments, the method comprises performing one or more steps in a solvent-free mechanochemical system. In some embodiments, the derivatizing step is performed in a solvent-free mechanochemical system. In some embodiments, the solvent-free mechanochemical system is free of organic solvents. In some embodiments, all of the steps of the methods described herein are free of organic solvents. However, not all of the steps of the methods described herein are required to be solvent free. For example, the purification, of the derivatized compounds can be performed with various solvents, including, but not limited to, organic solvents, and the like.

In some embodiments, the solvent-free mechanochemical system is a mill. The mill can provide energy to the system that would otherwise normally be provided by heat or other forms of energy. Examples of mills include, but are not limited to, shaker-type ball mill, a planetary mill, or an attritor mill. The mechanochemical system or device can be any system or device that imparts sufficient mechanical energy to the compounds in the mixture so as to temporarily liquefy the component having the lowest melting point. In some embodiments, the only compound that is temporarily liquefied is the compound with the lowest melting point.

The methods described herein can be used to isolate, separate or purify a plurality of compounds from a mixture. In some embodiments, the mixture comprises 2, 3, 4, 5, 6, 7, 8, 9, or 10 compounds, or a number of compounds ranging between any two of these values. In some embodiments, the mixture comprises at least 2, 3, 4, 5, 6, 7, 8, 9, or 10 compounds.

Accordingly, in some embodiments, a method is provided wherein the mixture comprises at least a third compound having a third melting point wherein the melting point of the second compound is lower than the melting point of the third compound. In some embodiments, the method comprises derivatizing In some embodiments, the method comprises derivatizing the second compound in a solvent-free mechanochemical process according to the methods described herein, replacing the first compound with the second (and so on in the case of multiple compounds), the second compound is selectively or preferably derivatized after the first compound has been substantially removed from the mixture. The temperature at which the derivatizing step occurs, however, can be different from the temperature at which the first compound was derivatized because it is based upon the melting point of the second compound and the eutectic point of the mixture, which may be altered after the first compound is substantially isolated or purified out of the mixture. In some embodiments, the second compound is derivatized at a temperature less than the melting point of the third compound. In some embodiments, the second compound is derivatized at a temperature less than the melting point of the second compound. In some embodiments, the second compound is derivatized at a temperature equal to or greater than the second melting point but less than the melting point of the third compound. After derivatizing the second compound, the second derivatized compound can be purified from the mixture. The process can then be repeated in an analogous method to purify further compounds from the mixture. Multiple serial processes can result in removal or purification of a number of different compounds from the mixture.

In some embodiments, a method of purifying a compound from a mixture of a plurality of compounds is provided. In some embodiments, the method comprises: a) providing a mixture of a plurality of compounds, each of the plurality of compounds having a different melting point, wherein the mixture comprises a first compound having a first melting point, wherein the first melting point has the lowest melting point of the different melting points of the plurality of the compounds; b) isolating the first compound having the lowest melting point by derivatizing the first compound having the lowest melting point of the plurality of compounds in a solvent-free mechanochemical process to produce a first derivatized compound, wherein the derivatizing step is performed at a temperature equal to or greater than the first melting point, but less than the next highest melting point of another compound present in the mixture of the plurality of compounds; and c) purifying the first derivatized compound from the mixture; and d) optionally repeating steps a)-c) to purify each compound present in the mixture of the plurality of compounds, wherein the compounds are purified in ascending order of melting point. In some embodiments, the derivatizing step is performed at a temperature less than a melting point of another compound present in the mixture, wherein the melting point of the another compound is higher than the first melting point. In some embodiments, the derivatizing step is performed at a temperature that is less than the melting point of the first melting point.

EXAMPLES

Example 1

Separation of Galactose and Xylose Derivatized with Acetic Acid

Reagent grade xylose (6.01 grams), galactose (7.30 grams), and acetic acid were purchased from Sigma Aldrich All chemicals were used without further purification. The reaction was run in a cylindrical stainless steel jar (236 mL, 76 mm diameter) sealed with a silicone robber gasket and a threaded lid. In a typical experiment, the jars were filled with the reagents and 12 stainless steel balls (½ inch diameter). To the reaction chamber three drops of concentrated sulfuric acid were added as a catalyst. After all reagents and balls were added, the jar was sealed and rolled at a rate of 47 rotations per minute at room temperature. The balls colliding with one another or the sides of the jar produced the mechanical energy to drive the mechanochemical reactions. After one, two, four, five and seven days the jar was opened and a small sample of the reaction mixture was removed mid stored at 4° C. in glass vials for future analysis.

The samples were then run on an HPLC within a 24 hour period at the end of the reaction. For the HPLC runs, small samples of the reaction mix tore were dissolved into water. This was filtered then directly injected into the HPLC with no further preparation. HPLC analysis showed that the sugars could be separated after being derivatized with acetic acid. The results demonstrated that xylose preferentially reacted before galactose in a mechanochemical reaction due to its lower melting point. Therefore, the method can be used to separate sugars from a mixture.

Example 2

Separation of Galactose and Xylose Derivatized with Ethyl Alcohol

Galactose (7.30 grams), Xylose (5.99 grams) and Ethyl Alcohol were reacted in the presence of hydrobromic acid (3 drops) according to the method described in Example 1. The samples were collected and analyzed on an HPLC according to the method described in Example 1. HPLC analysis showed that the sugars could be separated after being derivatized with ethyl alcohol. The results demonstrated that xylose preferentially reacted before galactose in a mechanochemical reaction due to its lower melting point. Therefore, the method can be used to separate sugars from a mixture.

Example 3

Separation of Galactose and Xylose Derivatized with Stearic Acid

Galactose, Xylose, and Stearic acid are reacted in the presence of sulfuric acid according to the method described in Example 1. The samples are collected and analyzed on an HPLC according to the method described in Example 1. HPLC analysis shows that the sugars are separated after being derivatized with ethyl alcohol. The results demonstrate that xylose preferentially reacts before galactose, in a mechanochemical reaction due to its lower melting point. Therefore, the method is used to separate sugars from a mixture.

Example 4

Separation of Galactose and Xylose Derivatized with Stearyl Alcohol

Galactose, Xylose, and Stearyl Alcohol are reacted in the presence of hydrobromic acid according to the method described in Example 1. The samples are collected and analyzed on an HPLC according to the method described in Example 1. HPLC analysis shows that the sugars are separated after being derivatized with ethyl alcohol. The results demonstrate that xylose preferentially reacts before galactose in a mechanochemical reaction due to its lower melting point.

Therefore, the method is used to separate sugars from a mixture.

Example 5

Serial Separation of at Least 3 Sugars from a Mixture

Into a 30 mL cup of a high energy planetary ball-mill galactose (3.0 g, mp. 167° C.), glucose (3.0 g, mp. 148° C.), mannose (3.0 g, mp. 133° C.), stearyl alcohol (4.5 g, mp. 60° C.) and one drop of HCl (1.0 M) is placed. In addition, five stainless steel balls (1.0 cm diameter) are added to the reaction mixture. The cup is then sealed and placed into the ball-mill at room temperature for one hour at 700 rpm. After this time, the crude reaction mixture is added to distilled water (100 mL) for which the galactose and glucose dissolved, but the crude acetal, which is the unpurified reaction product produced by reacting mannose and stearyl alcohol product (about 7.5 g) did not. The aqueous portion is completely dried then added back into another ball mill cup. To this mixture, comprising primarily galactose and glucose, stearyl alcohol (4.5 g) and one drop of HCl (1.0 M) is added. The cup is then sealed and placed into the ball-mill for one hour at 700 rpm and heated to 35° C. After this time, the crude reaction mixture is added to distilled water (100 mL) for which the galactose dissolved, but the crude acetal product (about 7.5 g) did not. Therefore, the method is used to perform serial separation of the sugars in the mixture.

Example 6

Purification of Amino Acids from a Mixture

Into a 30 mL cup of a high energy planetary ball-mill an amino acid (A) having a high lattice energy (3.0 g), an amino acid (B) having a medium lattice energy (3.0 g), an amino acid (C) having a low lattice energy (3.0 g) and stearic acid (8.5 g, mp. 60° C.) are placed. In addition, five stainless steel balls (1.0 cm diameter) are added to the reaction mixture. The cup is then sealed and placed into the ball-mill at room temperature for one hour at 700 rpm. After this time, the crude reaction, mixture is added to distilled water (100 mL) for which amino acids A and B dissolved, but the crude amide product (about 11.5 g) did not. The aqueous portion is completely dried then added back into another ball mill cup. To this mixture, comprising primarily amino acids A and B, stearic acid (8.5 g) is added. The cop is then sealed and placed into the ball-mill for one hour at 700 rpm and heated to 35° C. After this time, the crude reaction mixture is added to distilled water (100 mL) for which amino acid A dissolved, but the crude amide product (about 13.5 g) did not. The method is used to separate amino acids based upon the differences in lattice energies.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method comprising: providing a mixture comprising a first compound and a second compound, wherein the first compound has a first melting point, the second compound has a second melting point, and the first melting point is lower than the second melting point; derivatizing the first compound in a solvent-free mechanochemical process to produce a first derivatized compound, wherein the derivatizing step is performed at a temperature less than the second melting point, wherein the solvent-free mechanochemical reaction is performed in a mill, wherein each of the first compound and the second compound is, independently, a carbohydrate, amino acid, lipid, hydrocarbon, nucleic acid, or peptide; and purifying the first derivatized compound from the mixture.

2. The method of claim 1, wherein the derivatizing step is performed at a temperature equal to or greater than the first melting point.

3. The method of claim 1, wherein the mill is a shaker-type ball-mill, a planetary mill, or an attritor mill.

4. The method of claim 1, wherein the derivatizing step is performed at room temperature.

5. The method of claim 1, wherein the carbohydrate is a C5 sugar or C6 sugar.

6. The method of claim 1, wherein the carbohydrate is arabinose, galactose, glucose, or mannose.

7. The method of claim 1, wherein the mixture is a black liquor.

8. The method of claim 7, wherein the black liquor comprises arabinose, galactose, glucose, mannose, or any combination thereof.

9. The method of claim 8, wherein the first compound is mannose.

10. The method of claim 1, wherein the first compound is mannose and the second compound is arabinose, galactose, or glucose.

11. The method of claim 1, wherein the derivatizing step comprises contacting the first compound with an acid or alcohol to produce the first derivatized compound.

12. The method of claim 1, wherein the purifying step comprises purifying the first derivatized compound by extraction, liquid chromatography, recrystallization, or any combination thereof.

13. The method of claim 1, wherein the purifying step comprises hydrolyzing the first derivatized compound to yield a first purified compound.

14. The method of claim 1, wherein the mixture comprises a third compound having a third melting point, wherein the second melting point is lower than the third melting point, the method further comprising: derivatizing the second compound in a solvent-free mechanochemical process to produce a second derivatized compound, wherein the derivatizing of the second compound is performed at a temperature less than the third melting point; and purifying the second derivatized compound from the mixture.

15. The method of claim 14, wherein the derivatizing of the second compound is performed at a temperature equal to or greater than the second melting point.

16. The method of claim 14, the method comprising recrystallizing the mixture prior to derivatizing the second compound.

17. The method of claim 14, wherein the derivatizing of the second compound comprises reacting the second compound with an acid or alcohol to produce the second derivatized compound.

18. The method of claim 11, wherein the acid or alcohol is stearic acid, stearic alcohol, acetic acid, ethyl alcohol, or methyl alcohol.

19. The method of claim 1, the method further comprising: derivatizing an additional compound with the lowest melting point after purifying the first derivatized compound to yield an additional derivatized compound, wherein the additional compound has a higher melting point than the first compound; and purifying the additional derivatized compound.

20. The method of claim 17, wherein the method is repeated until all of the compounds in the mixture are purified, wherein the compounds are purified in order of their ascending melting point temperatures.

21. A method of purifying a compound from a mixture of a plurality of compounds, the method comprising:
   a) providing a mixture of a plurality of compounds, each of the plurality of compounds having a different melting point, wherein the mixture comprises a first compound having a first melting point, wherein the first melting point has the lowest melting point among the different melting points of the plurality of the compounds;
   b) isolating the first compound having the lowest melting point by derivatizing the first compound having the lowest melting point of the plurality of compounds in a solvent-free mechanochemical process to produce a first derivatized compound, wherein the derivatizing step is performed at a temperature less than a melting point of an another compound present in the mixture, wherein the melting point of the another compound is higher than the first melting point, wherein the solvent-free mechanochemical reaction is performed in a mill, wherein each of the first compound and the another compound is, independently, a carbohydrate, amino acid, lipid, hydrocarbon, nucleic acid, or peptide; and
   c) purifying the first derivatized compound from the mixture;
   d) optionally repeating steps a)-c) to purify each compound present in the mixture of the plurality of compounds, wherein the compounds are purified in ascending order of melting point.

22. The method of claim 21, wherein the mixture is a black liquor comprising arabinose, galactose, glucose, and mannose.

23. The method of claim 17, wherein the acid or alcohol is stearic acid, stearic alcohol, acetic acid, ethyl alcohol, or methyl alcohol.

* * * * *

UNITED STATES PATENT AND TRADEMARK OFFICE
CERTIFICATE OF CORRECTION

Page 1 of 2

PATENT NO. : 8,691,975 B2
APPLICATION NO. : 13/637249
DATED : April 8, 2014
INVENTOR(S) : Tapsak It is certified that error appears in the above-identified patent and that said Letters Patent is hereby corrected as shown below:

Delete the title page and substitute therefor with the attached title page consisting of new illustrative figure inserted on the front page of patent.

In the Specification

In Column 1, Line 3, below Title, insert -- CLAIM OF PRIORITY --.

In Column 3, Line 65, delete "efficient, and cost," and insert -- efficient and cost --, therefor.

In Column 4, Line 24, delete "hot not" and insert -- but not --, therefor.

In Column 4, Line 42, delete "purification," and insert -- purification --, therefor.

In Column 6, Line 11, delete "mid" and insert -- and --, therefor.

In Column 6, Line 51, delete "galactose," and insert -- galactose --, therefor.

In Column 7, Lines 42-43, delete "reaction," and insert -- reaction --, therefor.

In Column 7, Line 52, delete "13.5 g)" and insert -- 11.5 g) --, therefor.

Signed and Sealed this
Third Day of February, 2015

Michelle K. Lee
*Deputy Director of the United States Patent and Trademark Office*

(12) United States Patent
Tapsak

(10) Patent No.: US 8,691,975 B2
(45) Date of Patent: Apr. 8, 2014

(54) SOLVENT-FREE MECHANOCHEMICAL PURIFICATION OF COMPOUNDS

(75) Inventor: Mark Allan Tapsak, Orangeville, PA (US)

(73) Assignee: Empire Technology Development LLC, Wilmington, DE (US)

(*) Notice: Subject to any disclaimer, the term of this patent is extended or adjusted under 35 U.S.C. 154(b) by 0 days.

(21) Appl. No.: 13/637,249

(22) PCT Filed: Jun. 4, 2012

(86) PCT No.: PCT/US2012/040727
§ 371 (c)(1),
(2), (4) Date: Sep. 25, 2012

(87) PCT Pub. No.: WO2013/184091
PCT Pub. Date: Dec. 12, 2013

(65) Prior Publication Data
US 2013/0324712 A1   Dec. 5, 2013

(51) Int. Cl.
*C07H 1/06* (2006.01)
(52) U.S. Cl.
CPC .................................... *C07H 1/06* (2013.01)
USPC ............................................................ 536/119
(58) Field of Classification Search
CPC ...................................................... C07H 1/06
USPC ...................................................... 536/119
See application file for complete search history.

(56) References Cited

U.S. PATENT DOCUMENTS

| | | |
|---|---|---|
| 4,316,852 A | 2/1982 | Blachford |
| 5,318,794 A | 6/1994 | Richards |
| 6,730,812 B2 | 5/2004 | Pecharsky et al. |
| 7,105,714 B2 | 9/2006 | Pecharsky et al. |
| 2007/0155677 A1 | 7/2007 | Heikkila et al. |
| 2010/0015028 A1 | 1/2010 | Johnson et al. |

OTHER PUBLICATIONS

Whistler et al. aldchydo-D-Galactose Heptaacetate and aldehydo-D-Xylose Hexaacetate from Acetolysis of Guaran and Xylan.*
Wu et al. Solid silica sulfuric acid (SSA) as a novel and efficient catalyst for acetylation of aldehydes and sugars. Tetrahedron 62:7995-7998, 2006.*
Pirie NW. The Hyperacetylation of Aldoses. Biochem J 30(3): 374-376, 1936.*
Whistler et al. aldchydo-D-Galactose Heptaacetate and aldehydo-D-Xylose Hexaacetate from Acetolysis of Guaran and Xylan. J Am Chem Soc 71:1476-1477, 1949.*
International Search Report and Written Opinion for PCT/US2012/040727 dated Aug. 21, 2012.
Korolev et al., Mechanochemical Transformations of the Crystalline Anomers of D-Glucose, *Chemistry for Sustainable Development* (2004), 3:339-346 (Abstract).
Lyakhov et al., Mechanochemical Synthesis of Organic Compounds and Composites with Their Participation, *Russian Chemical Reviews* (2010), 79(3):189-203 (Abstract).
Medvedeva et al., Structural Transformations of Siberian Larch Arabinogalactan at Mechanochemical Treatment and Biological Properties of Products, *Chemistry of Plant Raw Material* (2009), 3:49-56 (Abstract).
Mugunthan et al., Application of Ball Milling Technology to Carbohydrate Reactions-II. Solvent-free Mechanochemical Synthesis of Glycosyl Azides, *Journal of Carbohydrate Chemistry* (2008), 27(5):294-299 (Abstract).
Patil et al., Application of Ball Milling Technology to Carbohydrate Reactions, Part 1. Regioselective Primary Hydroxyl Protection of Hexosides and Nucleoside by Planetary Ball Milling, *ChemInform* (Dec. 18, 2008), 40(3) (Abstract).
Patil et al., Solvent-free synthesis of thioglycosides by ball milling, *Green Chem.* (Apr. 24, 2009), 11:953-956 (Abstract).
Rothenberg et al., Understanding Solid Solid Organic Reactions, *J. Am. Chem. Soc.* (Aug. 16, 2001), 123(36):8701-8708 (Abstract).
Wang et al., Facile Preparation of Peracetates and Per-3-bromobenzoates of α-Mono- and Disaccharides, *Molecules* (Oct. 31, 2005), 10:1325-1334.

* cited by examiner

*Primary Examiner* — Brandon Fetterolf
*Assistant Examiner* — Yih-Horng Shiao
(74) *Attorney, Agent, or Firm* — Pepper Hamilton LLP

(57) ABSTRACT

Methods for purifying and extracting compounds from a mixture are provided using a solvent-free mechanochemical method. Methods for purifying and/or extracting sugars, amino acids, and, the like, from a mixture are also provided, using a solvent-free mechanochemical method.

23 Claims, 2 Drawing Sheets

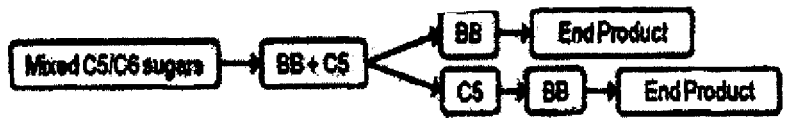

C6 sugars are first converted to building blocks, then after separation, C5 sugars are converted.

Similar to previous pathway, however, C5 sugars are converted first.